United States Patent [19]

Barrett et al.

[11] 4,023,036
[45] May 10, 1977

[54] APPARATUS AND METHOD FOR TRANSVERSE TOMOGRAPHY

[75] Inventors: Harrison H. Barrett; Scott Gordon, both of Tucson, Ariz.

[73] Assignee: University Patents, Inc., Stamford, Conn.

[22] Filed: June 16, 1975

[21] Appl. No.: 587,352

[52] U.S. Cl. .................... 250/237 R; 250/445 T; 356/167
[51] Int. Cl.² .................. H01J 39/12; G01N 23/04
[58] Field of Search ......... 356/71, 167; 250/237 R, 250/236, 313, 360, 322, 323, 445 T; 235/181

[56] References Cited
UNITED STATES PATENTS

| | | | |
|---|---|---|---|
| 3,483,557 | 12/1969 | Skenderhoff et al. | 235/181 |
| 3,621,222 | 11/1971 | Minami | 235/181 |
| 3,642,350 | 2/1972 | Hirsch et al. | 235/181 |
| 3,706,881 | 12/1972 | Emshwiller | 235/181 |
| 3,882,482 | 5/1975 | Green et al. | 235/181 |

*Primary Examiner*—Alfred E. Smith
*Assistant Examiner*—David K. Moore
*Attorney, Agent, or Firm*—Martin Novack

[57] ABSTRACT

An apparatus and method for generating a two-dimensional back-projected image of a slice of an object. In accordance with the invention there is provided a carrier means having a plurality of substantially parallel elongated projections thereon, each projection having an optical characteristic (transmissivity or reflectivity) representing the density characteristic of said slice of the object as measured at a particular relative rotational angle. Means are provided for imaging successive sinusoidal patterns on the carrier means, the successive sinusoidal patterns being imaged at a predetermined rate. Photodetector means are responsive to the imaged sinusoidal patterns. Finally, a display or recording means, synchronized at the predetermined rate, is responsive to the output of the photodetector for displaying the back-projected image. In a preferred embodiment of the invention the carrier means is a cylindrical film having projections thereon with transmissivities that represent the density characteristic of the slice of the object under consideration. In this embodiment, means are provided for uniformly illuminating the projections and optical mask means are provided in spaced relation to the cylindrical film and operative to image portions of the projections on the cylindrical film. Means are provided for rotating the cylindrical film on its axis so that the mask means continuously images different groups of projections on the film. Means are also provided for effecting relative angular motion between the mask means and the axis of the cylindrical film, whereby the mask means continuously images varying portions of the cylindrical film, the variation being along the axial direction thereof. In this embodiment the display means is synchronized with the rotational rate of the cylindrical film and with the effective angular displacement rate between the mask means and the axis of the cylindrical film.

30 Claims, 12 Drawing Figures

PRIOR ART

FIG. 1

PRIOR ART

$g_i(X) = f_i(X) \otimes h(X)$

FILTER FUNCTION h + MASK h – MASK

APPARATUS AND METHOD FOR TRANSVERSE TOMOGRAPHY

BACKGROUND OF THE INVENTION

This invention relates to X-ray tomography and, more particularly, to an apparatus and method for imaging cross-sections of objects using transverse tomography techniques. The subject matter of this invention is related to subject matter disclosed in U.S. application Ser. No. 587,329, entitled "Apparatus For Obtaining One-Dimensional Projections" filed of even date herewith and assigned to the same assignee as the present application and now abandoned.

Using conventional X-ray imaging techniques, a shadow view of a body under examination can be produced, but it does not contain information concerning the depth of details in the body. In many cases it is not possible to distinguish small objects since they are obscured by the structures of larger objects; e.g., bones. This drawback has been overcome to some degree by the development of body-section radiography techniques known as X-ray tomography.

Radiographic transverse tomography attempts to view sections or "slices" which are perpendicular to the axis of a patient. In a "classical" transverse tomographic system, incident X-radiation is passed through an object being studied at an angle and is imaged on a film. In order to image a particular slice, both the film and the object are rotated synchronously during the X-ray exposure. Shadows of points in a single plane of the object are continually projected on to the same place on the film during the rotation, whereas shadows of other parts of the object move in relation to the film. Thus, while the slice of interest is imaged relatively sharply, the resultant picture is overlayed by the motion-blurred images of other parts of the object. As a consequence, the resultant "tomogram" tends to lack contrast and fine detail is obscured.

Recently, digital processing techniques have been applied to the tomographic imaging problem and a degree of success has been achieved whereby blurred images of overlying and underlying planes have been removed so as to permit detection of greater detail. However, digital methods require the processing of extremely large quantities of data, and even fast computers take significantly long times to do the necessary computations. Accordingly, commercial computer tomography equipment is extremely expensive and beyond the financial reach of many who desire it.

In another type of transaxial tomography, a narrow beam of X-rays is employed and only the rays passing through the desired cross-section are incident on a film so, ideally, only information about the particular slice is recorded. The result is a so-called "one-dimensional projection". A plurality of one-dimensional projections can be obtained by passing X-rays through the same cross-section at a number of different rotational angles. The resultant set of one-dimensional projections can be processed optically. Alternatively, the values of each projection can be fed to a computer for digital analysis, whereby the density function of each elemental area in the plane is computed by one of a number of mathematical techniques which utilize iteration, mathematical filtering techniques, and other known solutions.

An early technique for optical processing of a set of one-dimensional projections is disclosed in U.S. Pat. No. 2,281,931 wherein a cylindrical lens system is utilized to optically "enlarge" each one-dimensional projection in a direction perpendicular to the plane of the section. Each enlarged one-dimensional projection is a two-dimensional image and the set of two-dimensional images which result from optically enlarging each one-dimensional projection are superposed with mutual angular displacements that correspond to the rotation angles at which the one-dimensional projections were originally taken. The image ultimately produced in this manner has been referred to as a "layergram" of the cross-section. In recent years, attempts have been made to process the layergram using spatial filtering methods of both optical and digital natures to restore the layergram image which is known to suffer blurring. However, the digital processing techniques again involve the handling and lengthy processing of large amounts of data, which is very expensive. Optical processing techniques toward this same end have generally been found to be either inadequate from a performance standpoint or unduly complex and expensive.

The techniques described in the above-referenced U.S. Pat. No. 2,281,931 is one of a number of image reconstruction techniques which utilize the "back-projection" of an image. Generally, the term "back-projection" infers that the value of a particular point in a projection is assigned to all points on a line perpendicular to the projection. The values of overlapping lines are integrated for all projections. The result is equivalent to back-projecting the values in each one-dimensional projection through the object and integrating their overall effect. As implied above, a simple back-projection yields results which are generally considered inadequate, and it is presently believed that a technique of back-projection, combined with a suitable filtering technique, could yield quality results. However, as emphasized above, such techniques have in the past required expensive and complex systems.

It is one object of the present invention to provide an improved relatively inexpensive apparatus for generating a filtered two-dimensional back-projected image of a plane or slice of an object by processing a set of one-dimensional projections of the object. It is a further object of the invention to provide an improved technique for initially obtaining the one-dimensional projections.

SUMMARY OF THE INVENTION

The present invention is directed to an improved apparatus and method for generating a two-dimensional back-projected image of a slice of an object. In accordance with the invention there is provided a carrier means having a plurality of substantially parallel elongated projections thereon, each projection having an optical characteristic (transmissivity or reflectivity) representing the density characteristic of said slice of the object as measured at a particular relative rotational angle. Means are provided for imaging successive sinusoidal patterns on the carrier means, the successive sinusoidal patterns being imaged at a predetermined rate. Photodetector means are responsive to the imaged sinusoidal patterns. Finally, a display or recording means, synchronized at the predetermined rate, is responsive to the output of the photodetector for displaying the back-projected image.

In a preferred embodiment of the invention the carrier means is a cylindrical film having projections thereon with transmissivities that represent the density characteristic of the slice of the object under consideration. In this embodiment, means are provided for uniformly illuminating the projections and optical mask means are provided in spaced relation to the cylindrical film and operative to image portions on the cylindrical film. Means are provided for rotating the cylindrical film on its axis so that the mask means continuously images different groups of projections on the film. Means are also provided for effecting relative angular motion between the mask means and the axis of the cylindrical film, whereby the mask means continuously images varying portions of the cylindrical film, the variation being along the axial direction thereof. In this embodiment the display means is synchronized with the rotational rate of the cylindrical film and with the effective angular displacement rate between the mask means and the axis of the cylindrical film.

Further features and advantages of the invention will become more readily apparent from the following detailed description when taken in conjunction with the accompanying drawings.

DESCRIPTION OF THE PREFERRED EMBODIMENT

Figure 1:
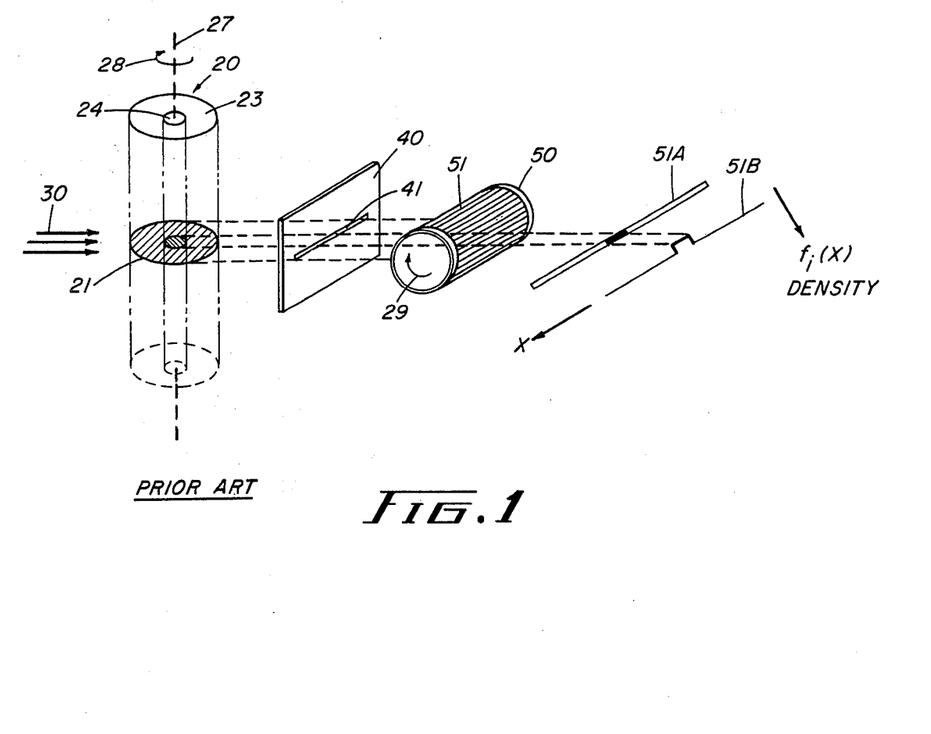
FIG. 1 is a diagrammatic representation of a technique for generating one-dimensional projections of a slice of an object.

FIG. 1 illustrates the nature of one-dimensional projections of a body cross-section or slice which can be obtained, for example, in accordance with a technique set forth in the above-referenced U.S. Pat. No. 2,281,931. A body 20, of which a cross-section 21 is to be reproduced, consists of an annular portion 23 of semi-transparent material, such as muscle tissue of a human limb, and a core portion 24 of a material which is less transparent to X-rays, such as bone. A beam of parallel X-rays 30 emanating from a remote source (not shown) passes through body 20, and a narrow portion of the X-ray beam, having a band-shaped cross-section, passes through a narrow elongated slot 41 in a diaphragm 40, which is typically formed of lead. The X-ray beam passing through slot 41 produces a narrow elongated image 51 on X-ray sensitive film member 50, which is provided in the shape of a cylinder. The image 51 can be considered as a one-dimensional projection whose optical characteristic corresponds to the different degrees of absorption of the X-rays by the portions 23 and 24 of the body 20 at section 21.

The elongated strip 51A at the right of FIG. 1 illustrates a simplified version of the one-dimensional projection 51 which is recorded on film 50. It is seen that the central portion of the projection is darkest due to the low transmissivity of core 24 to X-rays and the resultant lesser exposure of the corresponding portion on film 50. (It should be noted that since the thickness of annular portion 23 increases toward the center, the overall transmissivity of this part will also decrease gradually toward the center of body 20 but, for ease of explanation, this gradation is not shown in the simplified illustration of strip 51A or the curve 51B which follows.) The curve 51B illustrates graphically the density function of the slice 21 as a function of length along slot 41, this length being indicated by the coordinate $x$. The density, indicated as $f_i(x)$, is seen to correspond to the relative transmissivity of the cross-section as a function of $x$; i.e., the inverse of the density characteristic.

Returning to the structural portion of FIG. 1, the body 20, and consequently also the section 21 thereof, are rotated about an axis 27 which is normal to the plane of section 21 at the point of rotation, the rotation being represented by curved arrow 28. The cylindrical film 50, which is typically mounted on a drum, is rotated on its axis in angular synchronism with the rotation of body 20. At each of a number of discrete rotational positions, the body and the film 50 are stopped and a one-dimensional projection is recorded (like strip 51A). Accordingly, after a full 360° of rotation the cylindrical film 50 will contain a "set" of one-dimensional projections, i.e., the various $f_i(x)$, each one-dimensional projection having an optical characteristic which represents the density characteristic of the section or slice 21 of the object 20 as measured at a particular relative rotational angle.

Figure 2:
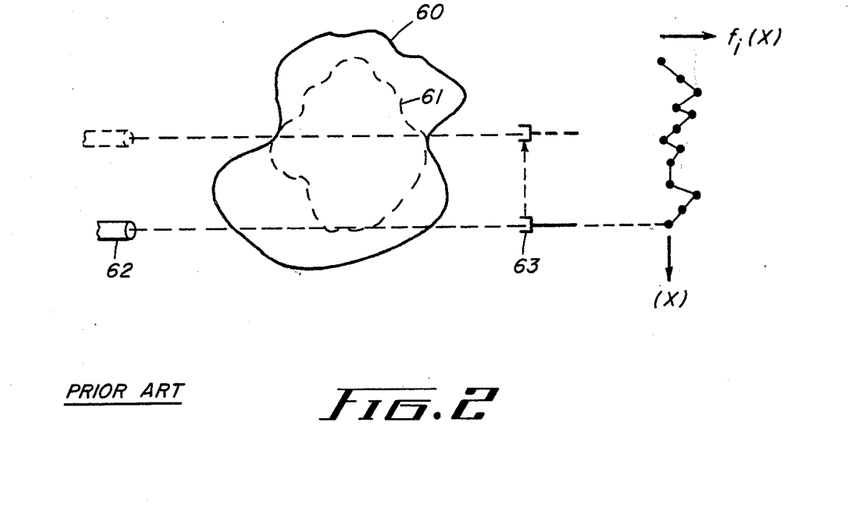
FIG. 2 shows another technique for obtaining one-dimensional projections of a slice of an object.

Referring to FIG. 2, there is shown another known technique of obtaining one-dimensional projections of a slice or section 61 of a three-dimensional body 60. A collimated "pencil" beam of X-rays is generated by a source 62, passed through the section 61, and received by a small-area scintillation detector 63, the output of which is indicated by a point on the graph at the right of FIG. 2. The source 62 and detector 63 are moved synchronously across the slice 61 and an output data value is obtained at each spaced position, each data point representing the intensity of the transmitted X-ray beam. The resultant function $f_i(x)$ is a one-dimensional projection similar in information content to those obtained using the system of FIG. 1, and as designated by the graph 51B of FIG. 1. It will be appreciated that, if desired, one could obtain an optical characteristic such as that of projection 51A from the data of FIG. 2 by utilizing the output of the detector 63 to modulate the intensity of a scanning beam exposing a film strip. More typically, the data points obtained from detector 63 are processed using a digital computer. A set of one-dimensional projections, $f_i(x)$, are obtained by taking the depicted measurements at a number of different rotational angles of the section 61, and the totality of the data is processed by a computer to attempt reconstruction of the elemental density function of the two-dimensional slice 61 of object 60. A problem of the system of FIG. 2 arises in maintaining registration and collimation when stepping the source and detector to different positions. An alternative technique employs a plurality of sources and/or detectors, but this requires precise balance of the multiple components as well as additional switching circuitry.

Figure 3:
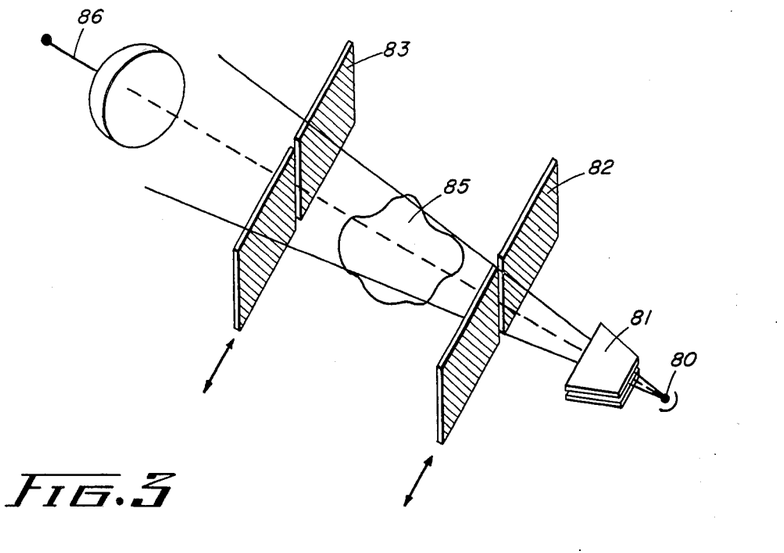
FIG. 3 is a schematic representation of an embodiment of an apparatus in accordance with the invention for obtaining one-dimensional projections of a slice of an object.
Figure 4:
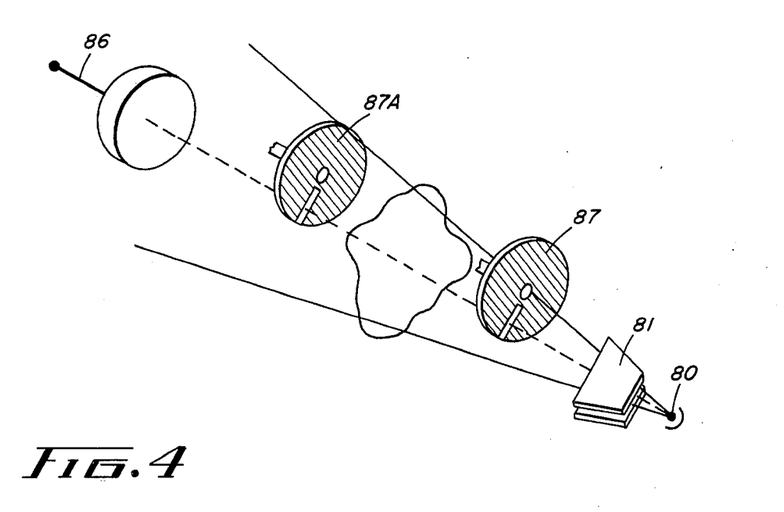
FIG. 4 is a schematic representation of another embodiment of an apparatus in accordance with the invention for obtaining one-dimensional projections of a slice of an object.

An apparatus in accordance with the invention for obtaining one-dimensional projections is shown in FIGS. 3 and 4. The embodiment of FIG. 3 uses a diverging X-ray beam from a source 80. A parallel-plate collimator 81 restricts the beam to a single plane. A pair of diaphragms 82 and 83 are each provided with a small slit and the two diaphragms are rectilinearly scanned in unison across the object 85 by suitable motive means 89. A single large-area detector 86, which needn't be position sensitive, receives the resultant two-dimensionally collimated beam and generates an output which is the desired one-dimensional projection as a function of the position of the slots in the diaphragms. In the embodiment of FIG. 4 a slit in the rotating disc 87 produces the desired beam as a function of slit position. Again, the output of the large-area detector, which may be a scintillating screen such as calcium tungstate or sodium iodide coupled to a photomultiplier, yields the desired one-dimensional projection. A second rotating disc with a slit, designated 87A, can be used to restrict scattered radiation. In both FIGS. 3 and 4 the scan can be stepped to a number of discrete positions or performed continuously. The output of the detector 86 can be coupled to a computer or optical characteristics like the strip 51A can be obtained by using a film at the detector position or modulating an unexposed film with obtained intensity measurements.

Figure 5:
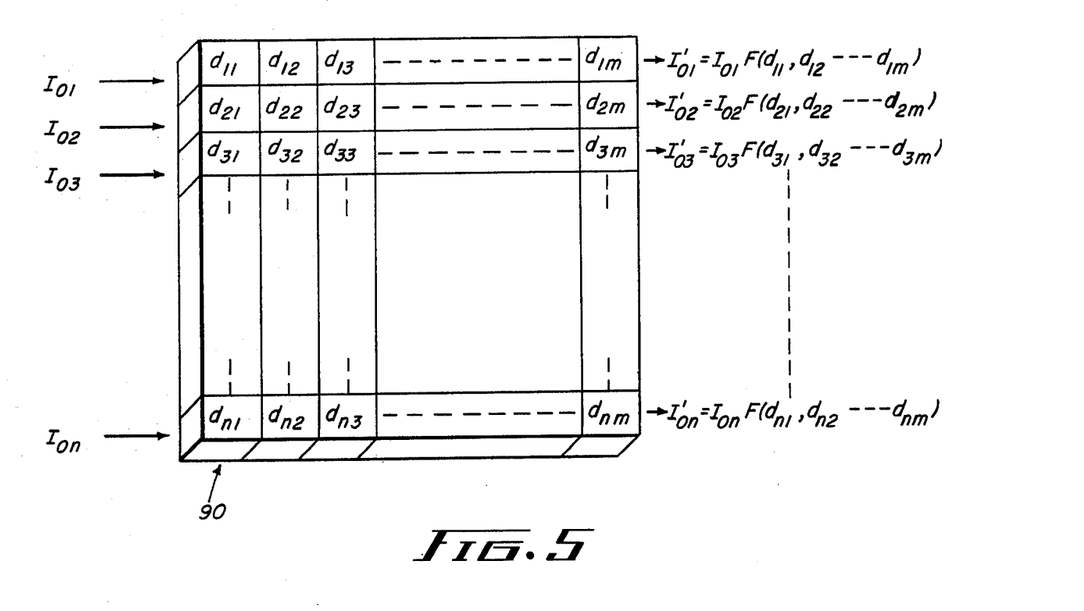
FIG. 5 is a diagram of a slice of an object useful in understanding approaches to obtaining the density characteristic of said slice.

FIG. 5 is helpful in further illustrating the nature of the obtained one-dimensional projections, as well as in understanding approaches to obtaining the density characteristics of a section or slice of an object from such projections, and especially approaches which utilize "back-projection". A thin section or slice 90 under investigation is depicted as being rectangular for ease of explanation. The section is divided into an array of small elemental units which comprise an $m$ by $n$ array wherein each element is designated by its position in the array and assumed to have a density which is to be ultimately determined. Thus, for example, the density of the element in the upper left hand corner is designated by $d_{11}$, its adjacent neighbor to the right has a density designated by $d_{12}$, and so on. The beam, or portion of the beam (e.g. in FIG. 2 or FIG. 1), passing through a particular row of elements is designated by I with two subscripts, the first subscript indicating the reference angle at which the X-ray energy is passed through the slice 90 (a 0° reference angle is shown in FIG. 5, so the first subscript is 0), and the second subscript indicating the relative position of the particular beam or beam portion along the one-dimensional data coordinate (e.g. the $x$ axis in FIGS. 1 and 2). The detected beams, or portions thereof, which have passed through the slice 90 are designated by primed versions of the input beams. Each output is equal to its corresponding input times a function of the elemental densities through which the beam or beam portion has passed. For example, it is seen that $I_{01}'$ is equal to $I_{01}$ times a function of the elemental densities of the first row of the array, as shown. Similarly, the remaining outputs are each also functions of the elemental densities in their corresponding rows. It will be appreciated that in the expressions for the one-dimensional projection values for a particular reference rotational angle (0° for the illustrated case), there are many more unknowns than equations. However, if the slice is now rotated on its axis to a number of different positions, and additional one-dimensional projection data values are obtained at each rotational angle, the full set of one-dimensional projections will yield a large number of equations which can be used to determine the unknowns; i.e., the individual elemental densities in the slice 90.

As referred to in the Background portion of the Specification, the set of one-dimensional projections can be processed by computer using various techniques. One type of prior art solution uses an iterative technique wherein assumed elemental density values are assigned to each member of the array. The computer calculates the output intensity values that would be obtained from the model, and these calculated output intensities are compared with the actual output intensities to obtain error values. The error values are examined and used to calculate appropriate modifications of the model which will yield smaller error values, and the process is continued until a model is obtained which yields error values that are considered acceptably small. Depending on the particular algorithm used, it will take at least some minimum number of computations for the model to converge to an acceptable state. In any event, the computer must have adequate speed, memory, etc. to obtain a solution within a reasonable time, so the equipment needed can be prohibitively expensive. A number of techniques have also been attempted wherein the computer systematically solves the simultaneous equations by classical means or employment of known matrix manipulation methods. Unfortunately, these approaches are also found to require very large numbers of calculations and expensive computer equipment is needed for solution within practical time constraints.

In the back-projection image reconstruction technique treated above, the value of a particular data point in a projection is assigned to all points on a line perpendicular to the projection. In terms of FIG. 5, for example, the value $I_{01}'$ would be assigned to each of the elements in the row to which that output intensity is attributed; viz., $d_{11}, d_{12} \ldots d_{1m}$. Similarly the output intensity value $I_{02}'$ is applied to all of the elemental densities in the second row; viz., $d_{21}, d_{22}, \ldots d_{2m}$, and so on for the remaining rows. Next, the output data values of the next one-dimensional projection are assigned in the same manner to each elemental density, and this is done for each relative rotation angle at which a one-dimensional projection was obtained. Thus, at the completion of the back-projection, each elemental density has a final value which equals the sum of all the data values attributable to it during the process previously described. The back-projection process can be performed either on a digital computer or optically, but the results of a simple back-projection have been found inadequate in most cases due to blurring.

Figure 6:
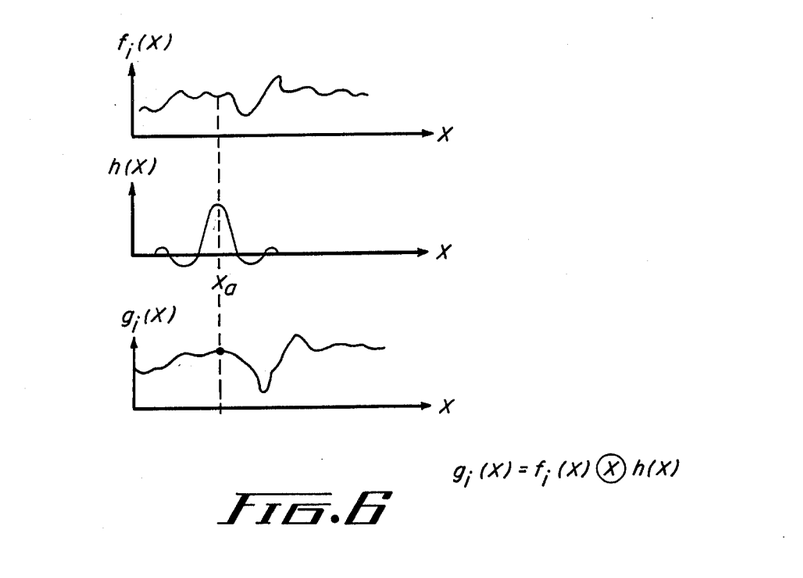
FIG. 6 shows graphs useful in describing the convolution of a filter function with a one-dimensional projection.

In order to derive better results using back-projection techniques, it has been suggested that a technique of "filtering" be used in conjunction with back-projection. The filtering can be thought of as a type of selective "weighting" which aids in restoration of a true density characteristic by removing blurring effects. The filtering can either be done on the one-dimensional projections before the back-projection operation, or it can be done on the reconstructed back-projected image. FIG. 6 illustrates the filtering of a particular one-dimensional projection designated $f_i(x)$ using a filter function designated by $h(x)$. Mathematically, the two functions $f_i(x)$ and $h(x)$ are convolved to obtain the resultant filtered one-dimensional projection which is designated $g_i(x)$. The convolution operation can be visualized graphically by considering the filter function $h(x)$ as being moved along the $x$ axis and a multiplication between $f_i(x)$ and $h(x)$ being performed at each point of the excursion of the filter function. For example, in FIG. 6 the filter function is shown at an abscissa position $x_a$ and the resultant data point on the function $g_i(x)$ (as shown by the dot on the third graph) is obtained by multiplying $h(x)$ at this position by the function $f_i(x)$. This operation is performed at each point along the $x$ axis and the function $g_i(x)$ is obtained in this manner. As disclosed in a publication of Cho et al in IEEE Transactions on Nuclear Science, Vol. NS-21, page 44 (June, 1974), one-dimensional projections are convolved with a processing function, as just described, the operation being performed on a digital computer.

The type of filtering and back-projection techniques just described, as well as those where convolution is performed after back-projection, involve large numbers of computations when performed on a digital computer, so expensive computing capability is required. Optical techniques have been attempted for performing these operations. For example, it is known that lenses perform Fourier transformation when coherent light is used. However, such systems tend to be limited by such factors as necessary photoreductions and film thickness variations.

Figure 7:
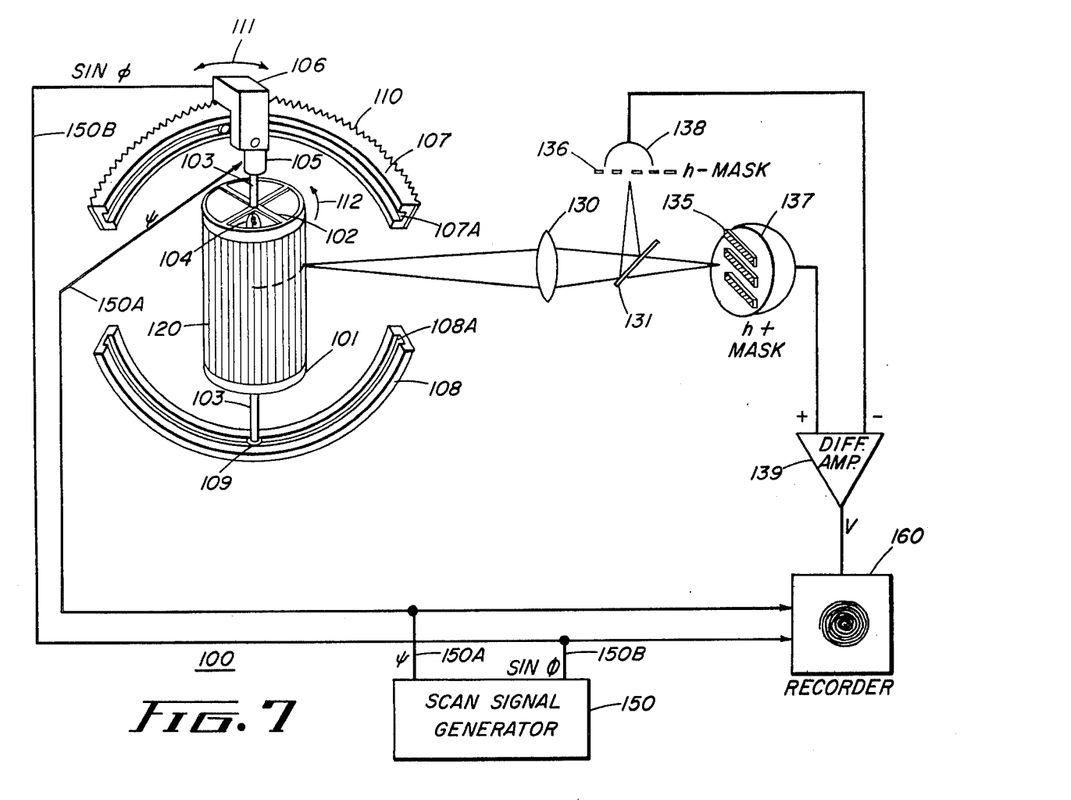
FIG. 7 is an elevational perspective view, partially in schematic block diagram form, of an apparatus in accordance with an embodiment of the invention.

Referring to FIG. 7, there is shown an embodiment of an apparatus 100 in accordance with the invention. A cylindrical drum 101, which may be formed of a suitable translucent material, such as a white plastic, is provided at its top and bottom ends with support ribs 102. Axially disposed members 103 are secured to the support ribs and protrude beyond the ends of drum 101. An elongated light source 104, which may comprise a long thin incandescent source (energized by means not shown) is mounted between the support ribs 102 along the axis of the drum. The light source provides substantially uniform illumination of the surface of the drum. The plastic surface of drum 101 acts as a light diffusor to insure the uniform illumination.

The upper axial member 103 is coupled to a small electric motor 105 which is, in turn, mounted on a bracket 106. The motor 105 is energized by a signal on a line 150A and causes relatively fast rotation of axial member 103 and, in turn, rotation of the drum 101 on its axis, as indicated by arrow 112. Upper and lower circular support members 107 and 108 are provided with central elongated slots 107A and 108A, respectively. The slot 107A receives a bearing of the bracket 106 and acts to guide the motion of the bracket and the slot 108A receives and retains an end bearing 109 therein. Mounted within bracket 106 is an additional electrical motor means (not visible) which is energized by a signal on line 150B. The motor within bracket 106 drives gearing which meshes with teeth 110 formed along the edge of the circular support member 107, and the motion of the gearing causes relatively slow movement of the bracket 106 which follows a path in one direction along the support 107 and then returns along the other direction in reciprocating fashion and as indicated by two-headed arrow 111. Accordingly, it is seen that the drum 101 spins at a relatively fast rate and tilts back and forth about its center at a relatively slow rate.

Mounted on the drum 101 is a film 120 which has recorded thereon a plurality of substantially parallel elongated projection images, each projection image having a transmissivity which represents the density characteristic of a cross-section or slice of an object as measured at a particular relative rotational angle. The film 120 may be recorded in the manner described in FIG. 1, or by using variations on techniques described in conjunction with FIGS. 2, 3 or 4. Each projection is of the general type described with reference to the strip 51A in FIG. 1, and the full 360° of arc of the film 120 contains adjacent projections taken at rotational increments of the object slice in question as it is rotated a full 360°.

In FIG. 7 the drum 101 is shown at an instant when it is in its vertical orientation. The optical receiving portion of the apparatus of FIG. 7 has its optical axis along the horizontal (i.e., perpendicular to the particular orientation of the drum shown in the FIG.). A lens 130 is representative of optics which receives and collects light from the film 120 and focuses the light at a pair of foci at which masks 135 and 136 are disposed, a beam splitter 131 effecting the division of the collected beam. The masks 135 and 136 achieve a filtering function of the type described in conjunction with FIG. 6, as will be described hereinafter. Large-area photodetectors 137 and 138 receive the light passing through masks 135 and 136, respectively, and generate output signals as a function of the received light intensity. The output of photodetector 138 is subtracted from the output of photodetector 137 by difference amplifier 139, whose output is a video signal designated "V". A scanning signal generator 150 generates output voltages on lines 150A and 150B which, it will be recalled, control the rate at which the drum 101 rotates and tilts. These signals also control the deflection circuitry of a display 160 (which could alternately be a recorder), so as to produce a spiral scan raster which has a radial component that varies in accordance with the signal on line 150B and a rotational component which varies in accordance with the signal on line 150A. The scanning beam of recorder or display 160 is modulated in accordance with the signal V and the resultant displayed or recorded image represents the filtered two-dimensional back-projected image of the slice of the object from which the one-dimensional projections on film 120 were originally made.

Figure 8:
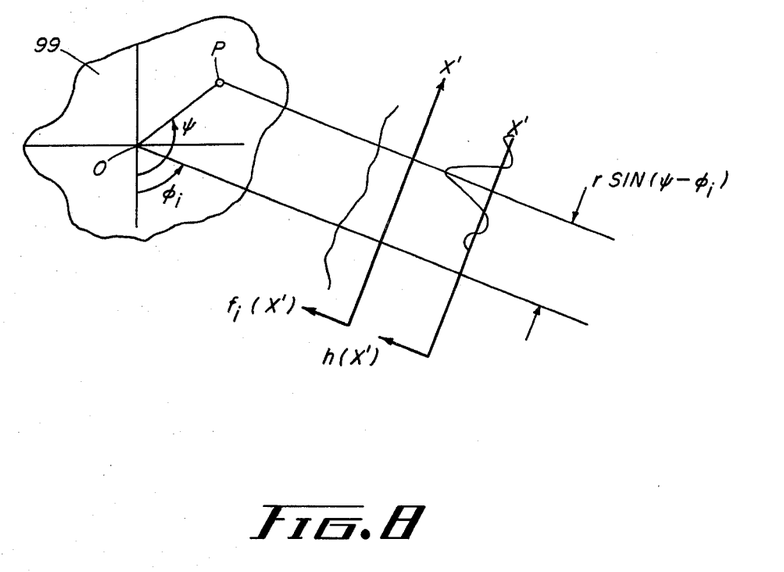
FIG. 8 is a representation of a slice of an object, along with explanatory graphs, which are useful in understanding the invention.
Figure 9:
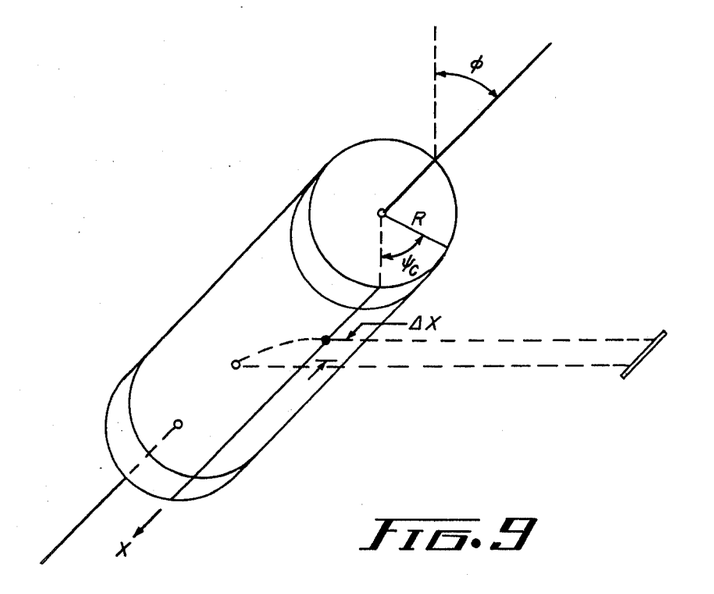
FIG. 9 is a simplified perspective representation of a portion of the invention which is useful in facilitating understanding of the invention.

An understanding of the operation of the apparatus of FIG. 7 is facilitated by FIGS. 8 and 9. (It can be noted at this point that some of the mathematics relating to techniques of transaxial tomography disclosed herein is set forth in the above-referenced publication of Cho et al. which describes the digital convolution of one-dimensional projections with a filter function.) Assume that $f_i(x)$ is the negative logarithm of a one-dimensional projection made at a reference rotational angle $\phi_i$, and assume further that the appropriate filtering function is designated $h(x)$ (see e.g. FIG. 6). A filtered projection can be represented by the following convolution integral:

$$\int_{-\infty}^{\infty} f_i(x-x')h(x')dx' \quad (1)$$

The desired complete filtered image can be obtained, as previously discussed, by back-projecting each of the filtered projections into the object space and summing over all $\phi_i$. Mathematically, this operation is described by the sum $$\Sigma \left[ \int_{-\infty}^{\infty} f_i(x-x')h(x')dx' \right]_{x=r\sin(\Psi-\phi_i)} \quad (2)$$

where $(r, \psi)$ are the polar coordinates of a point in the object that is being reconstructed. In FIG. 8, 0 is the center of rotation of the object slice 99 and P is a particular reconstruction point. As indicated, $\phi_i$ is the particular reference rotational angle at which the one-dimensional projection $f_i(x')$ is taken, and it is seen that $x=r\sin(\psi-\phi_i)$. It can be noted that for any one point $(r, \psi)$ it is not necessary to know the full convolution integral, but only its specific value for one displacement $x=r\sin(\psi-\phi_i)$.

Applicants have discovered that the mathematical operation of summation (2) can be performed using incoherent optics by employing the spinning and tilting cylindrical film setup of FIG. 7. The geometrical rationale can be better understood from FIG. 9 which shows the film-carrying drum titled at an angle $\phi$ with respect to the vertical. For purposes of FIG. 9, assume that the drum is sighted along the optical axis through a single slit (rather than the mask arrangement of FIG. 7). The portion of the drum surface seen through the slit will approximate the intersection of a plane with the cylindrical drum surface, the plane passing through the center of the drum. Accordingly, an element on each of half of the one-dimensional projection images on the drum will be viewed through the slit at any given instant. In FIG. 9, only a single one-dimensional projection is depicted, and the point on this particular one-dimensional projection which is "seen" through the slit is indicated by the dark dot. It can be shown that the displacement of the points (i.e., the point on the one-dimensional projection shown as well as on all other one-dimensional projections seen through the slit) with respect to the slit is given by $$\Delta x = R\sin\phi \sin(\psi_c - \phi_i) \quad$$

where R is the radius of the cylindrical drum, $\psi_c$ is the rotational angle of a data point under consideration, $\phi$ is the tilt angle with respect to the vertical, and $\phi_i$ is the relative rotational angle at which the one-dimensional projection containing a data point under consideration was taken (again, FIG. 8). Accordingly, by setting $\psi=\psi_c$ and $R\sin\phi = r$, the displacement $\Delta x$ is seen to be equivalent to the required shift in the convolution integral represented by expression (2). In the setup of FIG. 7, the integration operation is carried out by the large-area photodetectors 137 and 138. The film 120 on FIG. 7 can be initially recorded with a substantially logarithmic transmission characteristic, as follows from the known essentially linear Hurter-Driffeld characteristic of photographic film.

Figure 10:
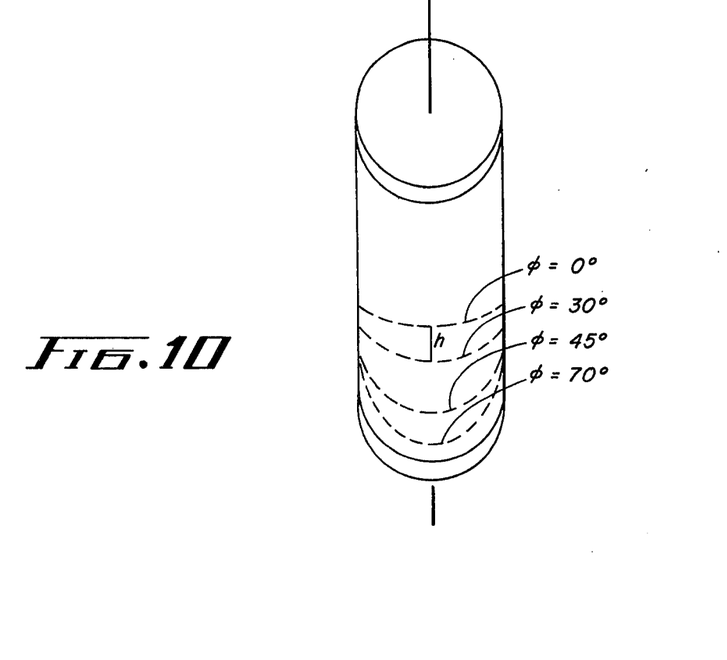
FIG. 10 is another simplified perspective representation of a portion of the invention which is useful in facilitating understanding of the invention.

FIG. 10 is intended to give further insight as to the sections on the film which are imaged through a simplified mask, such as the slit used in describing the model of FIG. 9. In FIG. 10 the optical axis is assumed to be perpendicular to the plane of the paper, and the top of the cylinder can be thought of as being tilted into the paper and away from the viewer. The dotted lines show the sections on the cylinder which are seen through a slit on the optical axis as the cylinder is tilted to various angles $\phi$. The sections of the cylindrical drum which are seen are intersections of planes with the tilted cylinder which result in elliptical sections on the cylinder and a corresponding sinusoidal pattern on the film. Only at the $\phi = 0°$ position shown in FIG. 7 will the imaged section be a circle. In all cases, the data points on a particular elliptical section being imaged will correspond to the totality of the back-projected contributions of a particular point P in the slice of the object under consideration (FIG. 8), the point P being defined by $r$ (which was seen above to equal $R\sin\phi$), $\psi$ and $\phi_i$. In operation of the system of FIG. 7, the cylindrical drum spins rapidly, varying $\psi$ (as controlled by the signal on line 150A) and therefore tracing out a circle in the reconstructed image. A relatively slower linear scan of $\sin\psi$ (the tilt rate being controlled by the signal on line 150B) varies the radius of the traced out circle, so a spiral is obtained, as is the case where the signals on lines 150A and 150B are utilized to control deflection circuits in display 160 in the manner indicated above.

Figure 11:
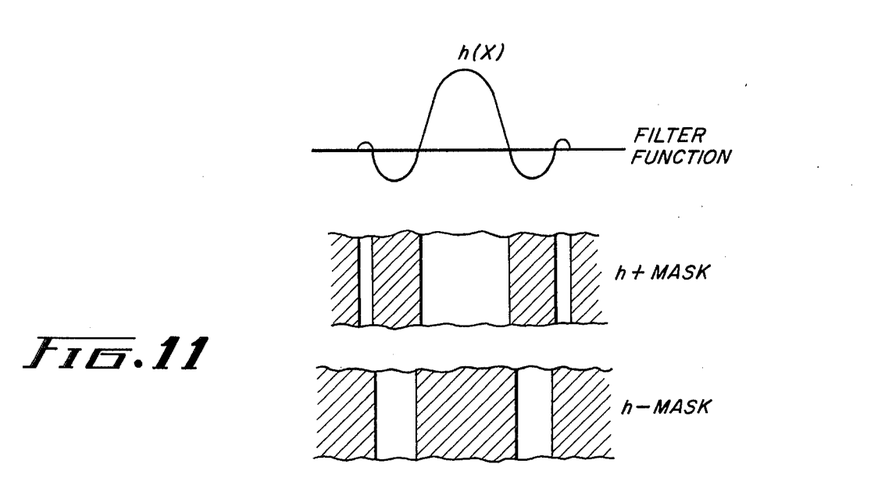
FIG. 11 shows the nature of the optical masks utilized in the embodiment of FIG. 7.

For purposes of understanding the manner in which the apparatus of FIG. 7 generates a back-projected image, the diagrams of FIGS. 9 and 10 substituted a simple slit for the masks 135 and 136 of FIG. 7, through which the cylindrical drum is actually viewed. FIG. 11 illustrates a type of mask which is suitable for use in the apparatus of FIG. 7. The filter function, $h(x)$, is shown in FIG. 11, is of the type described in conjunction with FIG. 6 and also shown diagramatically in the explanatory FIG. 8. The masks represent the filter function as a photographic transparency, and since $h(x)$ takes on both positive and negative values, two separate transparencies are utilized to represent a positive and negative parts of $h(x)$. The following equations show how $h(x)$ is represented by the $h_+(x)$ and $h_-(x)$ mask functions:

$$h_+(x) = \begin{cases} 0 \text{ if } h(x) < 0 \\ h(x) \text{ if } h(x) > 0 \end{cases}$$

$$h_-(x) = \begin{cases} -h(x) \text{ if } h(x) < 0 \\ 0 \text{ if } h(x) > 0 \end{cases}$$

$$h(x) = h_+(x) - h_-(x)$$

The masks of FIG. 11 utilize binary approximations of the filter function $h(x)$. For example, the relatively large central transparent portion of the $h_+(x)$ mask and the two relatively thin transparent adjacent portions of this mask relate in size to the areas under the positive portions of the $h(x)$ function, whereas the two transparent portions of the $h_-(x)$ mask are related in size to the area under the negative portions of the $h(x)$ curve. The desired bipolar output is obtained as the output of differential amplifier 139, which generates the difference between the light intensity seen through the two masks. From FIG. 8, it can be envisioned how the masks effectively achieve the desired convolution for each point being reconstructed.

Figure 12:
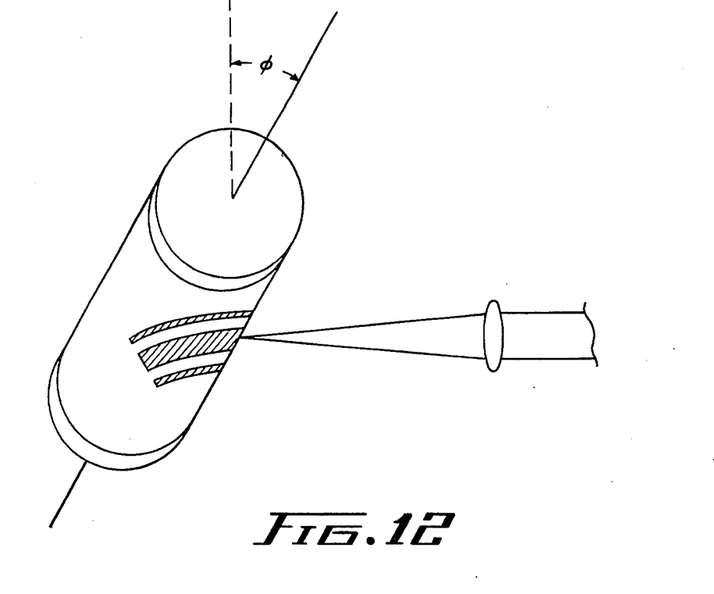
FIG. 12 is another simplified perspective representation of a portion of the invention which is useful in facilitating understanding of the invention.

FIG. 12 illustrates the sections on cylindrical drum 101 which are seen through the $h_+(x)$ mask at a tilted orientation of the cylindrical drum (the seen portions being shown shaded). The shaded elliptical sections are seen to correspond in thickness and spacing to the transparencies of the $h_+(x)$ mask. Thus, it can be visualized how the optical system of FIG. 7 performs the desired filtering and back-projection operations simultaneously by optically selecting appropriate sinusoidal patterns on the film (corresponding to elliptical sections on the cylinder) having transparencies which represent the original one-dimensional projections of the object slice being studied.

The invention has been described with reference to specific embodiments, but it will be understood that variations within the spirit and scope of the invention will occur to those skilled in the art. For example, the rotation and/or translation of the optical elements could be employed as an alternate form of achieving the desired result. Also, one or more suitable masks having a continuous grey-scale transmissivity could be substituted for the binary approximation masks disclosed.

We claim:

1. Apparatus for generating a two-dimensional back-projected image of a slice of an object, comprising:
   carrier means having a plurality of substantially parallel elongated projections thereon, each projection having an optical characteristic representing the density characteristic of said slice of the object as measured at a particular relative rotational angle;
   means for imaging successive sinusoidal patterns on said carrier means;
   photodetector means responsive to the imaged sinusoidal patterns; and
   display means responsive to the output of said photodetector means for displaying the back-projected image.

2. Apparatus as defined by claim 1 wherein said optical characteristic of the projections is transmissivity.

3. Apparatus as defined by claim 1 wherein successive sinusoidal patterns are imaged at a predetermined rate and said display means is synchronized at said predetermined rate.

4. Apparatus as defined by claim 1 wherein said means for imaging comprises an optical mask.

5. Apparatus as defined by claim 4 wherein said mask has an optical transmission characteristic which corresponds to a filter function.

6. Apparatus as defined by claim 2 wherein said means for imaging comprises an optical mask.

7. Apparatus as defined by claim 1 wherein said means for imaging comprises a pair of optical masks having transmission characteristics corresponding to the positive and negative portions of a filter function.

8. Apparatus as defined by claim 1 wherein said carrier means comprises an illuminated cylindrical film.

9. Apparatus as defined by claim 8 wherein said means for imaging comprises an optical mask.

10. Apparatus for generating a two-dimensional back-projected image of a slice of an object, comprising:
    a cylindrical carrier having a plurality of substantially parallel elongated projections thereon in the axial direction, each projection having an optical characteristic representing the density characteristic of said slice of the object as measured at a particular rotational angle;
    means for uniformly illuminating said carrier;
    optical mask means spaced from said cylindrical carrier and operative to image portions of projections on said cylindrical carrier;
    means for rotating said cylindrical carrier on its axis whereby said mask means continuously images different groups of projections on said cylindrical carrier;
    means for effecting relative angular motion between said mask means and the axis of said cylindrical carrier whereby said mask means images varying portions of said cylindrical carrier, the variations being along the axial direction thereof;
    photodetector means responsive to the image viewed through said mask means; and
    display means responsive to the output of said photodetector means for displaying the back-projected image of said slice.

11. Apparatus as defined by claim 10 wherein said optical characteristic of the projections is transmissivity.

12. Apparatus as defined by claim 10 wherein said means for effecting relative angular motion between said mask means and the axis of said cylindrical carrier comprises means for tilting the axis of said cylindrical carrier.

13. Apparatus as defined by claim 10 wherein said display means is synchronized with the rotational rate of said cylindrical carrier.

14. Apparatus as defined by claim 10 wherein said mask means has an optical transmission characteristic which corresponds to a filter function.

15. Apparatus as defined by claim 10 wherein said optical mask means comprises a pair of optical masks having transmission characteristics corresponding to the positive and negative portions of a filter function.

16. Apparatus as defined by claim 10 wherein said cylindrical carrier comprises a film mounted on a translucent drum.

17. Apparatus as defined by claim 10 wherein said varying portions on said cylindrical carrier are elliptical in shape.

18. Apparatus as defined by claim 17 wherein said means for effecting relative angular motion between said mask means and the axis of said cylindrical carrier comprises means for tilting the axis of said cylindrical carrier.

19. A method for generating a two-dimensional back-projected image of a slice of an object, comprising the steps of:
    providing a plurality of substantially parallel elongated projections on a carrier, each projection having an optical characteristic representing the density characteristic of said slice of the object as measured at a particular relative rotational angle;
    imaging successive sinusoidal patterns on said carrier;
    detecting the intensity of the imaged sinusoidal patterns; and
    displaying the back-projected image as a function of the detected intensity.

20. A method for generating a two-dimensional back-projected image of a slice of an object, comprising the steps of:

providing a plurality of substantially parallel elongated projections on a cylindrical carrier in the axial direction on said carrier, each projection having an optical characteristic representing the density characteristic of said slice of the object as measured at a particular rotational angle;

uniformly illuminating said carrier;

providing optical mask means spaced from the cylindrical carrier and operative to image portions of projections on said cylindrical carrier;

rotating said cylindrical carrier on its axis whereby said mask means continuously images different groups of projections on said cylindrical carrier;

effecting relative angular motion between said mask means and the axis of said cylindrical carrier whereby said mask means images varying portions of said cylindrical carrier, the variations being along the axial direction thereof;

detecting the intensity of the image viewed through said mask means; and displaying the back-projected image of said slice as a function of the detected intensity.

21. The method as defined by claim 20 wherein the step of effecting relative angular motion between said mask means and said cylindrical carrier comprises tilting the axis of said cylindrical carrier.

22. Apparatus for generating a two-dimensional back-projected image of a slice of an object from carrier means having a plurality of substantially parallel elongated projections thereon, each projection having an optical characteristic representing the density characteristic of said slice of the object as measured at a particular relative rotational angle, comprising:

means for imaging successive sinusoidal patterns on said carrier means;

photodetector means responsive to the imaged sinusoidal patterns; and display means responsive to the output of said photodetector means for displaying the back-projected image.

23. Apparatus as defined by claim 22 wherein said optical characteristic of the projections is transmissivity.

24. Apparatus as defined by claim 22 wherein successive sinusoidal patterns are imaged at a predetermined rate and said display means is synchronized at said predetermined rate.

25. Apparatus as defined by claim 22 wherein said means for imaging comprises an optical mask.

26. Apparatus as defined by claim 25 wherein said mask has an optical transmission characteristic which corresponds to a filter function.

27. Apparatus as defined by claim 23 wherein said means for imaging comprises an optical mask.

28. A method for generating a two-dimensional back-projected image of a slice of an object from a plurality of projections on a carrier, each projection having an optical characteristic representing a physical characteristic of said slice of the object as measured at a particular relative rotational angle, comprising the steps of:

a. imaging a pattern on said carrier, said pattern substantially corresponding to the positions on said carrier which represent the contributions to said projections from a particular elemental unit in the slice of the object;

b. detecting the intensity of the imaged pattern;

c. displaying the detected intensity at a display position which corresponds with the position of the particular elemental unit; and d. repeating steps (a) through (c) for other elemental units in the slice of the object.

29. The method as defined by claim 28 wherein said physical characteristic is density.

30. The method as defined by claim 28 wherein said projections are substantially parallel elongated projections and said patterns are sinusoidal patterns of different amplitude and/or phase.

* * * * *

UNITED STATES PATENT OFFICE
CERTIFICATE OF CORRECTION

PATENT NO. : 4,023,036
DATED : May 10, 1977
INVENTOR(S) : Harrison Barrett et al.

It is certified that error appears in the above-identified patent and that said Letters Patent are hereby corrected as shown below:

col. 6, lines 11, 12 "unknows" should be --unknowns--.

col. 10, line 55 change "$h(x) - h_+(x) - h_-(x)$"

to --$h(x) = h_+(x) - h_-(x)$--.

Signed and Sealed this twenty-third Day of August 1977

[SEAL]

Attest:

RUTH C. MASON
Attesting Officer

C. MARSHALL DANN
Commissioner of Patents and Trademark